United States Patent
Baeumert et al.

(10) Patent No.: US 6,921,545 B2
(45) Date of Patent: Jul. 26, 2005

(54) SYNERGISTIC CONTROL OF PESTS

(75) Inventors: Klaus Baeumert, Frankfurt am Main (DE); Heinz-Joachim Belt, Burgwedel (DE)

(73) Assignee: Solvay Fluor und Derivate GmbH, Hannover (DE)

( * ) Notice: Subject to any disclaimer, the term of this patent is extended or adjusted under 35 U.S.C. 154(b) by 0 days.

(21) Appl. No.: 10/655,130

(22) Filed: Sep. 5, 2003

(65) Prior Publication Data

US 2004/0047914 A1 Mar. 11, 2004

Related U.S. Application Data

(63) Continuation of application No. PCT/EP02/02222, filed on Mar. 1, 2002.

(30) Foreign Application Priority Data

Mar. 6, 2001 (DE) .......................................... 101 10 570

(51) Int. Cl.$^7$ ........................ A01N 59/24; A01N 25/00; A01N 59/02; A01N 59/10
(52) U.S. Cl. ...................... 424/612; 424/405; 424/613; 424/703
(58) Field of Search ................................ 424/405, 612, 424/673, 703

(56) References Cited

U.S. PATENT DOCUMENTS 6,279,261 B1  8/2001  Binker et al.

FOREIGN PATENT DOCUMENTS

| DE | 19706842 A1 * | 8/1998 |
| DE | 19709914 | 9/1998 |
| DE | 19732575 | 2/1999 |
| DE | 19747640 | 5/1999 |
| WO | 93/13659 | 7/1993 |
| WO | 02/074089 | 9/2002 |

OTHER PUBLICATIONS

R. H. Scheffrahn, et al., "Synergism of methyl bromide and sulfuryl fluoride toxicity against termites (isoptera: kalyermitidae, rhinotermidtidae) by admixture with carbon dioxide" Journal of Economic Entomology, vol 88, No. 3, Jun. 1995, pp. 649–653.
Database WPI, Article No. XP002204389, Feb. 6, 2001.
Database WPI, Article No. XP002204388, Oct. 7, 1997.
E. Kenaga, et al., "Some Biological, Chemical and Physical Properties of Sulfuryl Fluoride as an Insecticidal Fumigant" *Journal of Economic Entomology*, 50(1), 1957, pp. 1–6.
E. Kenaga, et al., "Time, Temperature and Dosage Relationships of Several Insecticidal Fumigants" *Journal of Economic Entomology*, 54(3), 1961, pp. 537–542.

* cited by examiner

*Primary Examiner*—S. Mark Clardy
*Assistant Examiner*—Frank Choi
(74) *Attorney, Agent, or Firm*—Crowell & Moring LLP

(57) ABSTRACT

Sulfuryl fluoride and ovicidal gases have been found to exert a synergistic action on insect eggs, so it is possible to fumigate under sublethal conditions relative to the ovicide, and the dose of ovicidal gas can be reduced e.g. to sublethal concentrations.

10 Claims, No Drawings

SYNERGISTIC CONTROL OF PESTS

CROSS REFERENCE TO RELATED APPLICATIONS

This application is a continuation of international patent application no. PCT/EP02/02222, filed Mar. 1, 2002, designating the United States of America, and published in German as WO 02 074089, the entire disclosure of which is incorporated herein by reference. Priority is claimed based on Federal Republic of Germany patent application no. DE 101 10 570.3, filed Mar. 6, 2001.

BACKGROUND OF THE INVENTION

The present invention relates to a method of pest control using a synergistically acting combination of gases.

It is known to use sulfuryl fluoride as a pesticide, see U.S. Pat. No. 2,875,127. The gas is suitable for controlling pests and fungi in wood used or not used in buildings, and also in freshly felled wood, for controlling beetles or termites, and for pest control in museums, churches, storage rooms or for example mill buildings. As is known from the publication by E. E. Kenaga in J. Econ. Entomol. 50 (1957) pages 1 to 6, a very high concentration of sulfuryl fluoride is necessary to control insect eggs. It has therefore already been proposed to combine sulfuryl fluoride with an ovicidal gas (German published application no. DE 197 09 914). Suitable ovicides include, for example, hydrocyanic acid, alkyl formates, alkyl isothiocyanates, nitrites, carbonyl sulfide or hydrogen phosphide.

SUMMARY OF THE INVENTION

It is an object of the present invention to devise an improved method by means of which reliable control of pests is possible. This object is achieved by the method and the mixture of substances with which reliable fumigation is possible, as described in further detail hereinafter.

The method according to the invention for reliable fumigation of rooms or objects attacked by pests simultaneously with sulfuryl fluoride and an ovicidal gas provides for sulfuryl fluoride and the ovicidal gas to be used under conditions which for sulfuryl fluoride and the ovicidal gas considered on their own are sublethal with respect to the extermination of insect eggs.

The term "reliable fumigation" means that all the life stages of the pests (eggs, larvae, pupae or adults) found in the rooms or objects attacked by the pests are substantially completely exterminated.

It is known to the person skilled in the art that the lethal dose with respect to insects is determined particularly by the following factors: the type of the insect; its stage of development; the concentration of the fumigation agent; the temperature; the duration of fumigation (see on this point also E. E. Kenaga, J. Econ. Entomol. 54(1961), pages 537–542). The longer the fumigation can last, and the higher the temperature at which the fumigation is carried out, the lower is the lethal concentration of the fumigation agent. The lethal concentration can be determined by tests as described by Kenaga. In practical application, however, it frequently has to be considered that there is an upper limit to the temperature, because corresponding energy costs make a great difference or sensitive objects must not be heated to too high a temperature. The duration of the fumigation may be limited for economic reasons. The minimum concentration for achieving an ovicidal action is regarded as 5 g/m$^3$ for hydrocyanic acid (HCN, hydrogen cyanide); see German published application nos. DE 197 32 575 and DE 197 09 914. A minimum concentration of 20 g/m$^3$ is quoted for methyl formate, 5 g/m$^3$ for carbonyl sulfide, 10 g/m$^3$ for acetonitrile, 5 g/m$^3$ for methyl isothiocyanate and 50 ppm for hydrogen phosphide (see German published application no. DE 197 09 914).

The method according to the invention provides that the ovicidal gas can be used under conditions which are sublethal with respect to the substantially complete extermination of the insect eggs. It is therefore possible to fumigate using a sublethal concentration of the ovicide, for example at a concentration which is at most 90%, preferably at most 80% and in particular at most 70% of the concentrations of the ovicidal agent which are lethal under the given conditions with respect to exterminating eggs. Alternatively or additionally, it is possible to reduce the fumigation time and/or to fumigate at a lower temperature. Preferably fumigation is carried out using sulfuryl fluoride and the ovicidal gas in concentrations which on their own are sublethal with respect to the extermination of insect eggs.

Preferred ovicidal gases include hydrocyanic acid, PH$_3$, alkyl formates, alkyl nitrites, alkyl isothiocyanates, carbonyl sulfide or methyl bromide. "Alkyl" here preferably stands for methyl or ethyl, in particular methyl.

The sulfuryl fluoride is used in a concentration which is lethal to developed stages of the insect (larva, pupa or adult). Such concentrations are sublethal with respect to the extermination of insect eggs. The concentrations of sulfuryl fluoride may however also be reduced somewhat, for example to at most 90% or even less of the concentration needed to exterminate the larvae, pupae or adults.

If different types of insect are being controlled, the concentrations relate to the insect which is most difficult to control.

The preferred ovicidal gas is hydrocyanic acid. Preferably the hydrocyanic acid is used in a concentration of at most 3 g/m$^3$, in particular at most 2.5 g/m$^3$, very particularly preferably in a concentration of at most 2 g/m$^3$.

The method according to the invention is carried out under conventional conditions. The temperature is advantageously in the range of 15 to 55° C. The duration of fumigation lies in the range of about 2 to about 136 hours. The rooms to be fumigated are advantageously sealed off or enveloped. Carbon dioxide may additionally be used because it has an advantageous effect on the effectiveness of fumigation agents.

For example vehicles, transport vehicles (ships, railway trucks, lorries), rooms in buildings (churches, museums, mills), storage rooms (grain stores, silos, bunkers or containers) and also individual enveloped objects such as works of art can be treated.

Advantageously, the water content in the air in the rooms to be treated is reduced, for example with commercially available dehumidifiers.

Sulfuryl fluoride and ovicidal gas may be used in a mixture or separately. The weight ratios of sulfuryl fluoride to the preferred ovicidal gases are compiled in the following table, the particulars each relating to 20 parts by weight sulfuryl fluoride.

TABLE 1

Maximum use of ovicidal gas in parts by weight, relative to 20 parts by weight $SO_2F_2$.

| | Hydrocyanic acid | Methyl formate | Methyl isothiocyanate | Carbonyl sulfide |
|---|---|---|---|---|
| Maximum | 4 | 16 | 4 | 4 |
| Preferred maximum | 3 | 12 | 3 | 3 |
| Particularly preferred maximum | 2.5 | 10 | 2.5 | 2.5 |
| in particular maximum | 2 | 8 | 2 | 2 |

The numbers quoted relate to the use of only one type of ovicidal gas. If a mixture is used, the particulars must be reduced corresponding to the content of the mixture. A 50:50 mixture of hydrocyanic acid and methyl formate will then be used in such a quantity that at most 2 parts by weight hydrocyanic acid and at most 8 parts by weight methyl formate are used per 20 parts by weight sulfuryl fluoride.

The invention also relates to mixtures which comprise or consist of sulfuryl fluoride and an ovicidal gas selected from the group consisting of hydrocyanic acid, methyl or ethyl formate, methyl isothiocyanate or carbonyl sulfide. In this case, the proviso applies that, if only one type of ovicidal gas is contained in the mixture, at most 4 parts by weight hydrocyanic acid, carbonyl sulfide or methyl isothiocyanate and at most 16 parts by weight methyl or ethyl formate are contained per 20 parts by weight sulfuryl fluoride. If two or more types of ovicidal gas are contained in a mixture, the proportion of the respective type of gas will be reduced correspondingly. For example, if hydrocyanic acid and methyl formate are contained in the same proportions by weight, at most 2 parts by weight hydrocyanic acid and at most 8 parts by weight methyl formate are contained in the mixture per 20 parts by weight sulfuryl fluoride.

The mixtures according to the invention may additionally contain auxiliaries such as carbon dioxide or warning gases. If the ovicidal gas is hydrocyanic acid, carbonyl sulfide or methyl isothiocyanate, mixtures in which at most 3 parts by weight, preferably at most 2.5 parts by weight, particularly preferably at most 2 parts by weight, of the ovicidal gas are contained per 20 parts by weight sulfuryl fluoride are preferred. In the case of alkyl formates, preferably at most 12 parts by weight are contained therein. For mixtures, what is stated above applies by analogy.

Preferred mixtures comprise $SO_2F_2$ and hydrocyanic acid as the ovicidal gas.

The invention has the advantage that it is possible to fumigate unter sublethal conditions with respect to the ovicidal gas. This means that it is possible to effect reliable extermination of the pests including any eggs present more quickly, with a lower gas concentration and/or at a lower temperature.

The following example is intended to explain the invention further, without limiting its scope.

EXAMPLES

Example

Fumigation with $SO_2F_2$/HCN Mixtures

General:
1. Insects Used

For each concentration batch and the untreated batches, 30 granary weevils Sitophilus granarius on wheat, granary weevil brood 1 (1 week old), 50 eggs of the Mediterranean flour moth Ephestia kuehniella and 30 red flour beetles Tribolium castaneum and brood mixture were used. The insects were caged in gauze tubes.

2. Time and Duration of the Fumigation

Each sample batch was fumigated for 48 hours at room temperature. Then the samples were placed in an atmosphere at 25° C. and 65–70% rel. humidity and monitored for 12 weeks.

3. Performance of the Tests

The samples were introduced into 2.5-liter gas washing bottles with a septum attachment. Then the corresponding quantity of gas was injected using a gas syringe. The gas was uniformly distributed in the bottles by means of a magnetic stirrer. After the injection, the bottles were allowed to stand for 48 hours. After aeration, the samples were placed in a climatic chamber and monitored weekly for further progeny.

4. Results

Both for the batch with 20 g $SO_2F_2/m^3$ and for the batch with 1.5 g $HCN/m^3$, offspring were produced, whereas for the batch with the combination of 20 g $SO_2F_2$ and 1.5 g $HCN/m^3$ no offspring were produced. This corresponds to a mortality of 100%. The control samples developed normally.

TABLE 2

Representation of the offspring in the fumigation test

| | | Tribolium castaneum 30 live beetles and brood | | Ephestia kuehniella (50 eggs) | | Stophilus granarius (30 live beetles on cereal) | | Sitophilus granarius (broodmixture) | |
|---|---|---|---|---|---|---|---|---|---|
| Dose | | Sample No. | Offspr. | Sample No. | Offspr. | Sample No. | Offspr. | Sample No. | Offspr. |
| $SO_2F_2$ + HCN | | 1 | 0 | 4 | 0 | 7 | 0 | 10 | 0 |
| 20 g/m³ 1.5 g/m³ | | 2 | 0 | 5 | 0 | 8 | 0 | 11 | 0 |
| (according to the invention) | | 3 | 0 | 6 | 0 | 9 | 0 | 12 | 0 |
| Control: | | | | | | | | | |
| $SO_2F_2$ | | 1a | 3 beetles | 4a | 0 | 7a | 1 beetle | 10a | 0 |
| 20 g/m³ | | 2a | 4 beetles | 5a | 0 | 8a | 2 beetles | 11a | 0 |
| | | 3a | 5 beetles | 6a | 0 | 9a | 9 beetles | 12a | 0 |

TABLE 2-continued

Representation of the offspring in the fumigation test

| Dose | Tribolium castaneum 30 live beetles and brood | | Ephestia kuehniella (50 eggs) | | Stophilus granarius (30 live beetles on cereal) | | Sitophilus granarius (broodmixture) | |
|---|---|---|---|---|---|---|---|---|
| | Sample No. | Offspr. | Sample No. | Offspr. | Sample No. | Offspr. | Sample No. | Offspr. |
| HCN 1.5/m³ | 1b | 9 beetles | 4b | 0 | 7b | 7 beetles | 10b | 0 |
| | 2b | 8 beetles | 5b | 0 | 8b | 5 beetles | 11b | 2 beetles |
| | 3b | 1 beetle | 6b | 0 | 9b | 11 beetles | 12b | 2 beetles |
| Untreated | U1 | 40 beetles | U3 | 23 moths | U5 | 46 beetles | U7 | 67 beetles |
| | U2 | 40 beetles | U4 | 34 moths | U6 | 25 beetles | U8 | 74 beetles |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method of fumigating a room or an object attacked by pests, said method comprising exposing the room or object to a gas comprising a lethal mixture consisting of a sublethal concentration of sulfuryl fluoride and a sublethal concentration of hydrocyanic acid, said hydrocyanic acid being present in a concentration of at most 3 g/m³.

2. A method according to claim 1, wherein the ovicidal gas is used in a concentration which corresponds to at most 70% of the lethal concentration.

3. A method according to claim 1, wherein the sulfuryl fluoride is used in a concentration which corresponds to at most 90% of the lethal dose with respect to larvae, pupae or adults.

4. A method according to claim 1, wherein hydrocyanic acid is used in a concentration of at most 2.5 g/m³.

5. A method according to claim 4, wherein hydrocyanic acid is used in a concentration of at most 2 g/m³.

6. An ovicidal gas comprising a lethal mixture consisting of a sublethal concentration of sulfuryl fluoride and a sublethal concentration of hydrocyanic acid, said gas comprising at most 4 parts by weight hydrocyanic acid per 20 parts by weight sulfuryl fluoride.

7. A mixture according to claim 6, further comprising carbon dioxide or a warning gas.

8. A mixture according to claim 6, comprising at most 3 parts by weight of hydrocyanic acid per 20 parts by weight sulfuryl fluoride.

9. A mixture according to claim 8, comprising at most 2.5 parts by weight of hydrocyanic acid per 20 parts by weight sulfuryl fluoride.

10. A mixture according to claim 9, comprising at most 2 parts by weight of hydrocyanic acid per 20 parts by weight sulfuryl fluoride.

* * * * *